United States Patent
Barthe et al.

(10) Patent No.: US 10,960,235 B2
(45) Date of Patent: **\*Mar. 30, 2021**

(54) ENERGY BASED HYPERHIDROSIS TREATMENT

(71) Applicant: Guided Therapy Systems, LLC, Mesa, AZ (US)

(72) Inventors: Peter G. Barthe, Phoenix, AZ (US); Michael H. Slayton, Tempe, AZ (US); Inder Raj S. Makin, Mesa, AZ (US)

(73) Assignee: Guided Therapy Systems, LLC, Mesa, AZ (US)

( \* ) Notice: Subject to any disclaimer, the term of this patent is extended or adjusted under 35 U.S.C. 154(b) by 332 days.

This patent is subject to a terminal disclaimer.

(21) Appl. No.: 16/049,364

(22) Filed: Jul. 30, 2018

(65) Prior Publication Data

US 2018/0333595 A1 Nov. 22, 2018

Related U.S. Application Data

(63) Continuation of application No. 15/243,081, filed on Aug. 22, 2016, now Pat. No. 10,046,181, which is a
(Continued)

(51) Int. Cl.
*A61N 7/02* (2006.01)
*A61B 8/00* (2006.01)
(Continued)

(52) U.S. Cl.
CPC .............. *A61N 7/02* (2013.01); *A61B 8/4281* (2013.01); *A61B 2017/320069* (2017.08);
(Continued)

(58) Field of Classification Search
CPC .... A61N 7/00; A61N 7/02; A61N 2007/0008; A61N 2007/0034; A61N 2007/0052;
(Continued)

(56) References Cited

U.S. PATENT DOCUMENTS

| 4,757,820 A \* | 7/1988 | Itoh .......................... A61N 7/02 600/439 |
| 6,450,979 B1 | 9/2002 | Miwa et al. |

(Continued)

FOREIGN PATENT DOCUMENTS

| EP | 2709726 | 11/2015 |
| EP | 1538980 | 1/2017 |

(Continued)

OTHER PUBLICATIONS

Adams et al., "High Intensity Focused Ultrasound Ablation of Rabiit Kidney Tumors" Sonablate High-Intensity Focused Ultrasound device; Journal of Endourology vol. 10, No. 1, (Feb. 1996).
(Continued)

*Primary Examiner* — Ronald Hupczey, Jr.
(74) *Attorney, Agent, or Firm* — Knobbe Martens Olson & Bear LLP

(57) ABSTRACT

A method and system for energy-based (e.g., ultrasound treatment and/or other modalities) of sweat glands are provided. An exemplary method and system for targeted treatment of sweat glands can be configured in various manners, such as through use of therapy only, therapy and monitoring, imaging and therapy, or therapy, imaging, and monitoring, and/or through use of focused, unfocused, or defocused ultrasound (or other energy) through control of various spatial and temporal parameters. As a result, ablative energy can be deposited at the particular depth at which the aberrant sweat gland population is located below the skin surface.

20 Claims, 20 Drawing Sheets

Related U.S. Application Data continuation of application No. 14/571,835, filed on Dec. 16, 2014, now Pat. No. 9,421,029, which is a continuation of application No. 13/950,728, filed on Jul. 25, 2013, now Pat. No. 8,932,224, which is a continuation of application No. 13/603,279, filed on Sep. 4, 2012, now Pat. No. 8,523,775, which is a continuation of application No. 13/444,485, filed on Apr. 11, 2012, now Pat. No. 8,282,554, which is a continuation of application No. 11/163,152, filed on Oct. 6, 2005, now abandoned.

(60) Provisional application No. 60/616,752, filed on Oct. 6, 2004.

(51) Int. Cl.
*A61B 17/32* (2006.01)
*A61B 18/00* (2006.01)
*A61N 7/00* (2006.01)

(52) U.S. Cl.
CPC ....... *A61B 2018/00005* (2013.01); *A61N 7/00* (2013.01); *A61N 2007/0004* (2013.01); *A61N 2007/0052* (2013.01); *A61N 2007/0078* (2013.01)

(58) Field of Classification Search
CPC .... A61N 2007/0056; A61N 2007/0065; A61N 2007/0082
See application file for complete search history.

(56) References Cited

U.S. PATENT DOCUMENTS

| | | | | |
|---|---|---|---|---|
| 6,595,934 B1* | 7/2003 | Hissong | ............... | A61N 7/02 601/3 |
| 6,645,145 B1 | 11/2003 | Dreschel et al. | | |
| 6,887,260 B1* | 5/2005 | McDaniel | ............ | A61B 18/203 607/88 |
| 7,491,171 B2* | 2/2009 | Barthe | ............... | A61B 8/546 600/439 |
| 8,282,554 B2* | 10/2012 | Makin | ............... | A61B 8/4281 600/439 |
| 8,333,700 B1* | 12/2012 | Barthe | ............... | A61N 7/02 600/439 |
| 8,523,775 B2* | 9/2013 | Barthe | ............... | A61B 8/4281 600/439 |
| 8,932,224 B2* | 1/2015 | Barthe | ............... | A61B 8/4281 600/439 |
| 9,421,029 B2* | 8/2016 | Barthe | ............... | A61B 8/4281 |
| 9,566,454 B2* | 2/2017 | Barthe | ............... | A61N 7/02 |
| 1,004,618 A1 | 8/2018 | Barthe et al. | | |
| 10,046,181 B2* | 8/2018 | Barthe | ............... | A61N 7/02 |
| 2005/0154332 A1* | 7/2005 | Zanelli | ............... | A61N 7/02 601/2 |
| 2008/0033458 A1 | 2/2008 | McLean et al. | | |
| 2016/0001097 A1 | 1/2016 | Cho et al. | | |
| 2018/0272156 A1 | 9/2018 | Slayton et al. | | |
| 2018/0272157 A1 | 9/2018 | Barthe et al. | | |
| 2018/0272158 A1 | 9/2018 | Barthe et al. | | |
| 2018/0272159 A1 | 9/2018 | Slayton et al. | | |

FOREIGN PATENT DOCUMENTS

| | | |
|---|---|---|
| EP | 2897547 | 11/2017 |
| WO | WO9939677 | 8/1999 |
| WO | WO2017127328 | 7/2017 |
| WO | WO2017149506 | 9/2017 |
| WO | WO2017165595 | 9/2017 |
| WO | WO2017212489 | 12/2017 |

OTHER PUBLICATIONS

Driller et al., "Therapeutic Applications of Ultrasound: A Review" IEEE Engineering in Medicine and Biology; (Dec. 1987) pp. 33-40.

Microchip microID 125 kHz EFID System Design Guide, Microchip Technology Inc. (2004).

Sonocare, Inc. Therapeutic Ultrasound System Model CST-100 Instruction Manual (1985).

Webster et al. "The role of ultrasound-induced cavitation in the 'in vitro' stimulation of collagen synthesis in human fibroblasts"; Ultrasonics pp. 33-37(Jan. 1980).

Ulthera, Inc., Petitioner Notice of Appeal to Federal Circuit 2018-1542 re: IPR2016-01459; 4 pages from [001] (no appendices) (Filed Feb. 9, 2018).

Federal Circuit Order Granting Ulthera Motion to Remand, re: 2018-1542; 4 pages [022] (Dated May 25, 2018).

* cited by examiner

ENERGY BASED HYPERHIDROSIS TREATMENT

CROSS-REFERENCE TO RELATED APPLICATIONS

This application is a continuation of U.S. application Ser. No. 15/243,081, filed Aug. 22, 2016, issued as U.S. Pat. No. 10,046,181, which is a continuation of U.S. application Ser. No. 14/571,835 filed on Dec. 16, 2014, issued as U.S. Pat. No. 9,421,029, which is a continuation of U.S. application Ser. No. 13/950,728 filed on Jul. 25, 2013, issued as U.S. Pat. No. 8,932,224, which is a continuation of U.S. application Ser. No. 13/603,279 filed on Sep. 4, 2012, issued as U.S. Pat. No. 8,523,775, which is a continuation of U.S. application Ser. No. 13/444,485 filed on Apr. 11, 2012, issued as U.S. Pat. No. 8,282,554, which is a continuation of U.S. application Ser. No. 11/163,152 filed on Oct. 6, 2005, now abandoned, which claims the benefit of priority to U.S. Provisional Application No. 60/616,752, filed on Oct. 6, 2004, each of which is incorporated in its entirety by reference herein. Any and all priority claims identified in the Application Data Sheet, or any correction thereto, are hereby incorporated by reference under 37 CFR 1.57.

BACKGROUND

Field of the Invention

This invention generally relates to a therapeutic ultrasound method and system, and more particularly, to a method and system for ultrasound treatment for superficial tissue containing sweat glands.

Description of the Related Art

The sweat glands in the body are of divided into apocrine and eccrine glands. Apocrine glands are similar to sebaceous glands, and are present mainly in the axillae. These glands, like sebaceous glands, secrete an oily proteinaceous product into the follicles. Bacterial digestion of apocrine sweat is largely responsible for underarm "body odor". Similarly, eccrine sweat glands are present deep in the dermis in the palms, soles and armpits and are responsible for temperature regulation resulting from sweating. Excessive activity of these glands also results in copious amounts of abnormal sweating ("hyperhidrosis"), primarily under autonomic neuronal control. Reduction of sweating from under the armpits and other regions is a particularly desirable effect within the modern society. Presently, chemical antiperspirants and deodorants are used frequently as a matter of personal hygiene. Antiperspirants are aluminum based salts that block the sweat gland ducts. The deodorant changes the pH of the skin milieu thereby minimizing the presence of (smell inducing) bacteria. The effects with both these components however, are temporary and these chemicals are known to irritate the skin in a good percentage of users.

Further, there is currently a significant unmet need in managing the excessive sweating and concomitant issues with odor as a result of Hydradenitis suppurativa (irritable infected armpit). This acne-like process in apocine follicles also causes hydradenitis suppurativa, which is often a devastating condition in which very painful cysts and scarring occurs repeatedly in the axillae. The etiology (causes) of this clinical condition is not well understood. However, there are a number of marginally effective approaches to manage this condition. Retinoid drug therapy works marginally but is associated with severe toxicity. Some prescription formulations of antiperspirants can be used, but they are not particularly effective. These preparations can be applied with the addition of an iontophoretic device. This technique however, is not known to be any more effective than the formulation. The sweat glands can be surgically removed from the armpits and/or the sympathetic nerve supply can be interrupted surgically. This approach is fraught with its own drawbacks in terms of morbidity, scarring and cost. BOTOX® is being used ever more for paralyzing the nerve connections that induce excessive sweating in the armpits. However, this is a new approach yet to be completely validated. This technique requires multiple injections (painful) and the results last a few months only (3-4 months), hence need to be repeated. This technique does not get rid of the odor associated with the condition.

SUMMARY OF THE INVENTION

The present invention describes a non-invasive method and system for using therapeutic ultrasound energy for the treatment of conditions resulting from sweat gland disorders. An ultrasound system and method comprises a transducer probe and control system configured to deliver ultrasound energy to the regions of the superficial tissue (e.g., skin) such that the energy can be deposited at the particular depth at which the aberrant sweat gland population is located below the skin surface.

In accordance with various exemplary embodiments, the ultrasound transducer can be driven at a number of different frequency regimes such that the depth and shape of energy concentration can match the region of treatment. In addition, the ultrasound source or beam radiated from the transducer can be highly focused, weakly focused, or divergent, each in a cylindrical or spherical geometric configuration, and/or can also be planar to radiate a directive beam through the tissue, or various other configurations. Further, the ultrasound field can be varied spatially and temporally in a suitable manner to achieve the optimal tissue effect and/or type of conformal lesion for treating the sweat glands.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various components and processing steps. It should be appreciated that such components and steps may be realized by any number of hardware components configured to perform the specified functions. For example, the present invention may be configured with various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to a method and system for sweat gland treatment as described herein are merely a few of the exemplary applications for the invention. For example, the principles, features and methods discussed may be applied to any medical or other tissue or treatment application.

In accordance with various aspects of the present invention, a non-invasive method and system for the treatment of sweat glands is described. In accordance with an exemplary embodiment, an ultrasound transducer probe and control system are configured to deliver ultrasound energy to a targeted/specified depth and zone where the sweat gland population is required to be treated. The ultrasound beam from the transducer probe can be spatially and/or temporally adjusted, modified or otherwise controlled to match the adequate treatment of the sweat glands in the region of interest.

Figure 1:
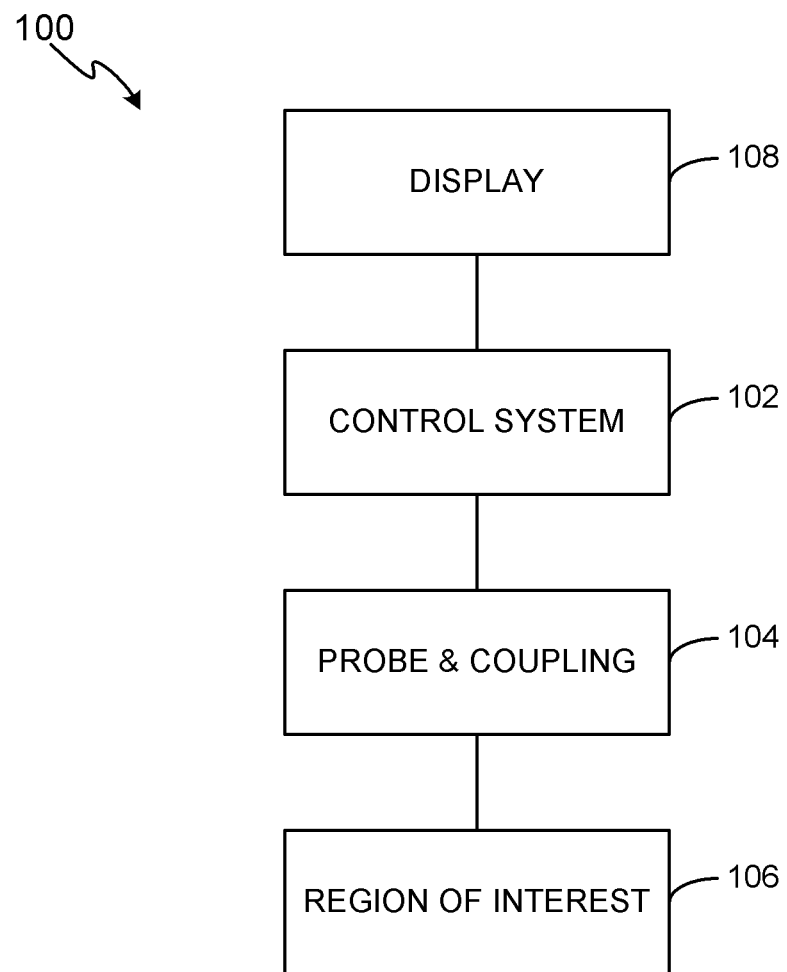
FIG. 1 illustrates a block diagram of an ultrasound therapy system for treating sweat glands in accordance with an exemplary embodiment of the present invention.

For example, in accordance with an exemplary embodiment, with reference to FIG. 1, an exemplary treatment system 100 configured to treat a region of interest (ROI) 106 comprises a control system 102, an imaging/therapy probe with acoustic coupling 104, and a display system 108.

Control system 102 and display 108 can comprise various configurations for controlling functionality of probe 104 and system 100, including for example a microprocessor with software and a plurality of input/output and communication devices, a system for controlling electronic and/or mechanical scanning and/or multiplexing of transducers, a system for power delivery, systems for monitoring, systems for sensing the spatial parameters and/or temporal parameters of the probe and transducers, and/or systems for handling user input and recording treatment input and results, among others. Imaging/therapy probe 104 can comprise various probe and/or transducer configurations. For example, probe 104 can be configured for a combined dual-mode imaging/therapy transducer, coupled or co-housed imaging/therapy transducers, a separate therapy probe and separate imaging probe, or a single therapy probe. In accordance with exemplary embodiments, imaging transducers may operate at frequencies from approximately 2 MHz to 75 MHz or more, while therapy energy can be delivered at frequencies from approximately 500 kHz to 15 MHz, with 2 MHz to 25 MHz being typical.

Figure 2A:
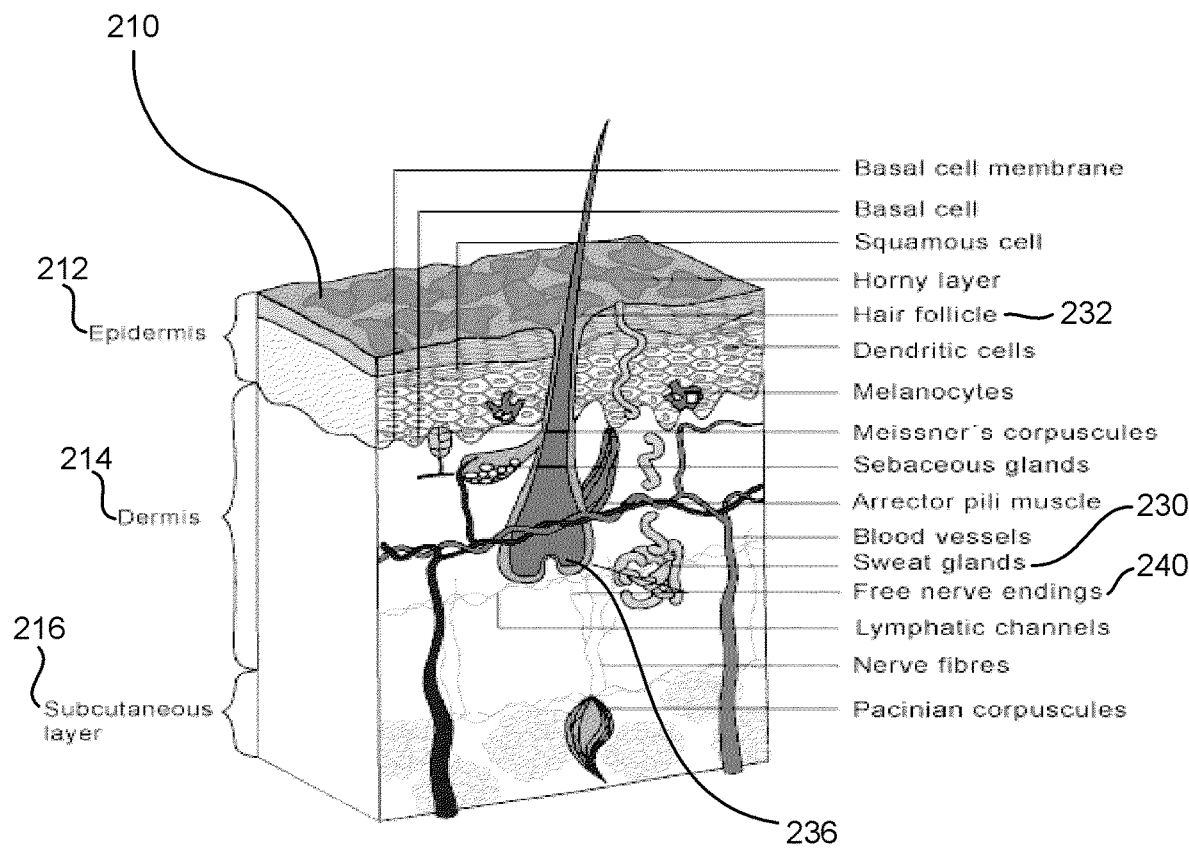
FIGS. 2A and 2B illustrate schematic diagrams of ultrasound treatment systems configured to treat the sweat glands via direct targeting of heating and damage within the treatment layer in accordance with various exemplary embodiments of the present invention.

With reference to FIG. 2A, sweat glands 230 are generally located within a dermis layer 214 at a depth close to hair bulbs 236. In order to treat sweat glands that require treatment in particular anatomical sites, such as, for example but not limited to, the axillary region (armpit), the palms and soles, an ultrasound transducer probe can be coupled to the skin tissue using one of the numerous coupling media, such as water, mineral oils, gels, and the like.

Figure 2B:
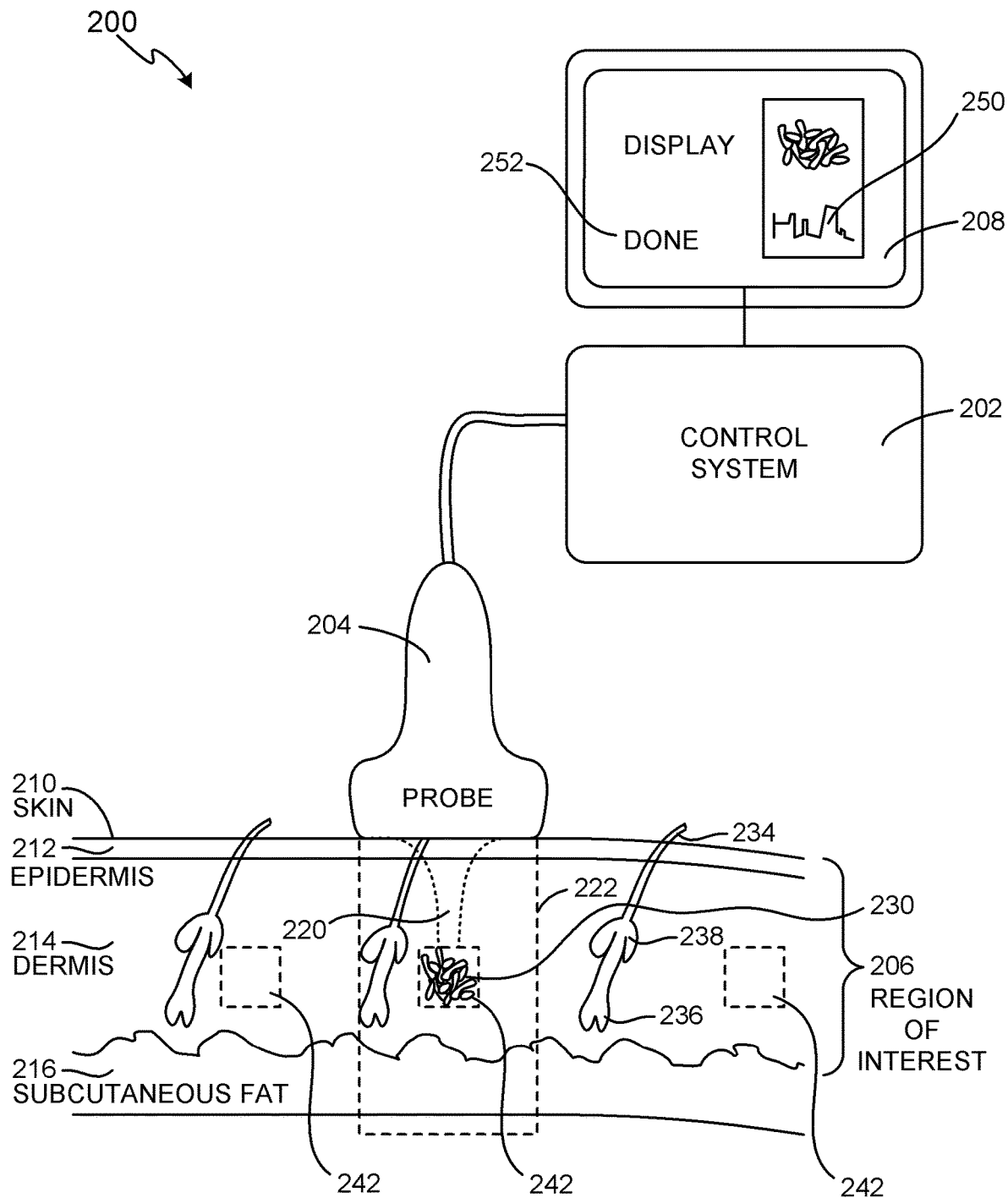

For example, with reference to FIG. 2B, in accordance with an exemplary embodiment an exemplary treatment method and system are configured for initially imaging a region 222 within a region of interest 206 and displaying that region 224 on a display 208 to facilitate localization of the treatment area and surrounding structures, e.g., identification of sweat glands 230, such as within the axillary region (armpit), the palms and soles or any other tissue or skin surrounding sweat glands. After localization, delivery of ultrasound energy 220 at a depth, distribution, timing, and energy level to achieve the desired therapeutic effect of thermal ablation to treat a sweat gland 230 is provided. Before, during, and/or after therapy, i.e., before, during and/or after delivery of ultrasound energy, monitoring of the treatment area and surrounding structures can be conducted to further planning and assessing of the results and/or providing feedback to control system 202 and a system operator.

In accordance with an exemplary embodiment, localization can be facilitated through ultrasound imaging that can be used to define the position of a sweat gland 230 and/or the depth of sweat glands 230 over a region of interest before depositing in a defined pattern at a target region 220. Such glands can be seen lying along hair follicles 232 and bulbs 236 and their image may be further enhanced via signal and image processing. Ultrasound imaging can also be used for safety purposes, namely, to avoid injuring vital structures, such as nerve endings 240. In accordance with other exemplary embodiments, localization can also be accomplished without imaging region 222, but instead can be based on prior known depths of sweat glands or other target regions, and thus be configured geometrically and/or electronically to selectively deposit energy at a particular known depth below skin surface 210 to a target region 220.

The ultrasound beam from probe 204 can be spatially and/or temporally controlled by changing the spatial parameters of the transducer, such as the placement, distance, treatment depth and transducer structure, as well as by changing the temporal parameters of transducer, such as the frequency, drive amplitude, and timing, with such control handled via control system 202. For example, in some applications, the temporal energy exposure at one location may range from approximately to 40 ms to 40 seconds, while the corresponding source frequency can suitably range from approximately 500 kHz to 15 MHz. Such spatial and temporal parameters can also be suitably monitored and/or utilized in open-loop and/or closed-loop feedback systems within treatment system 200. As a result of such spatial and/or temporal control, conformal lesions of various, specifically targeted, shapes, sizes and orientations can be configured within target region 220.

In accordance with an exemplary embodiment, the treatment resulting from ultrasound energy delivery in the region of sweat glands 230 can be used to achieve selective ablation of regions of sub-epidermal region (0.5-10 mm diameter zones). For example, one or more treated zones 242 can be configured to produce regions of ablative damage in spatially defined patterns, such as a discrete locus of spaced treatment spots or two- or three-dimensional matrix of damage or destroyed tissue, e.g., a matrix of cross-stitched, ellipsoidal/cigar-shaped, wedge-shaped, mushroom-shaped or any other conformal lesions, rather than heating and destroying the entire volume of the target layer of tissue. In such a treatment where surrounding regions are spared of damage, the surrounding undamaged tissue aids rapid healing and recovery.

In accordance with another exemplary embodiment, a whole contiguous sheet of treatment area can be achieved, whereby all the sweat glands within the said area are ablated. In addition to selective treatment of sweat gland regions, in accordance with another exemplary embodiment, treatment system 200 could be configured to "carpet bomb" the fat layer at 1-7 mm depth, e.g., up to 90% of the sweat glands in the armpit can be ablated without any physiologic issues.

In accordance with another exemplary embodiment of the present invention, an exemplary monitoring method may comprise monitoring the temperature profile or other tissue parameters of the region of interest 206, such as attenuation, speed of sound, or mechanical properties such as stiffness and strain of the treatment region and suitably adjust the spatial and/or temporal characteristics and energy levels of the ultrasound therapy transducer of probe 204. The results of such monitoring techniques may be indicated on display 208 by means of one-, two-, or three-dimensional images of monitoring results 250, or may simply comprise a success or fail-type indicator 252, or combinations thereof. Additional treatment monitoring techniques may be based on one or more of temperature, video, profilometry, and/or stiffness or strain gauges or any other suitable sensing technique.

The non-thermal effects from an acoustic field can also "shock" the sweat producing apocrine and eccrine cells in to reduced activity. These effects mentioned here as examples are, but not limited to, acoustic cavitation, acoustic streaming, inter-cellular shear effects, cell resonant effects, and the like.

In accordance with an exemplary embodiment, focused or directive ultrasound energy can be used for the treatment of sweat glands in the armpit (without the combination of pharmacological formulations). For example, a clinical indication would be to use in the management of Hidradenitis suppurativa. Ultrasound energy deposited at a selective depth can also be used in combination with a number of pharmaceutical formulations that are currently prescribed for the treatment of sweat gland hyperactivity in the axillary region, palms and soles. The ultrasound energy delivered to the target region in combination with the pharmaceutical agents such as BOTOX® or retinoids can help synergistically treat the sweat gland region by, (1) increasing activity of the agents due to the thermal and non-thermal mechanisms, (2) reduced requirement of overall drug dosage, as well as reducing the drug toxicity, (3) increase local effect of drug in a site selective manner.

Figure 3A:
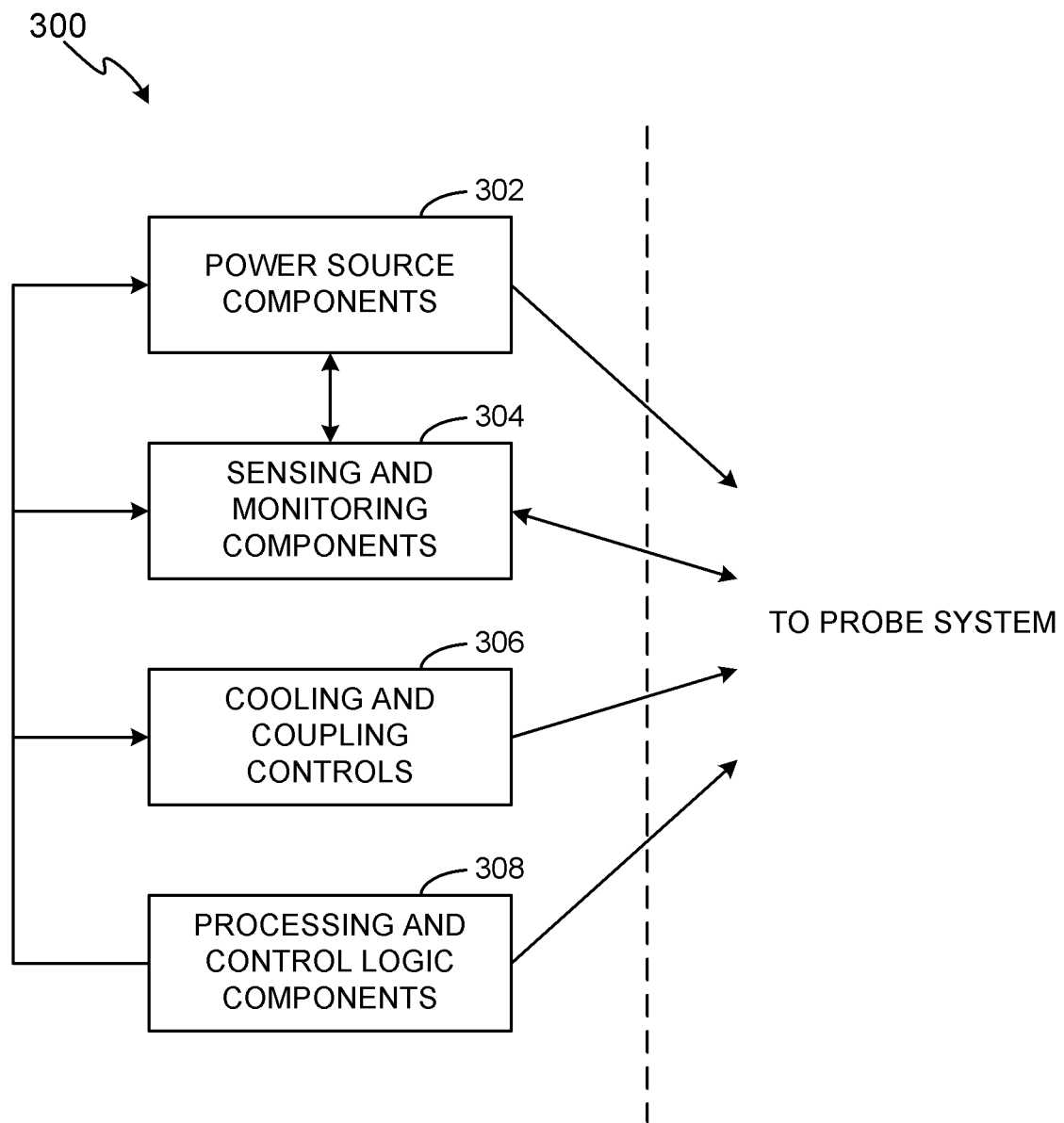
FIGS. 3A and 3B illustrate block diagrams of an exemplary control system in accordance with exemplary embodiments of the present invention.
Figure 3B:
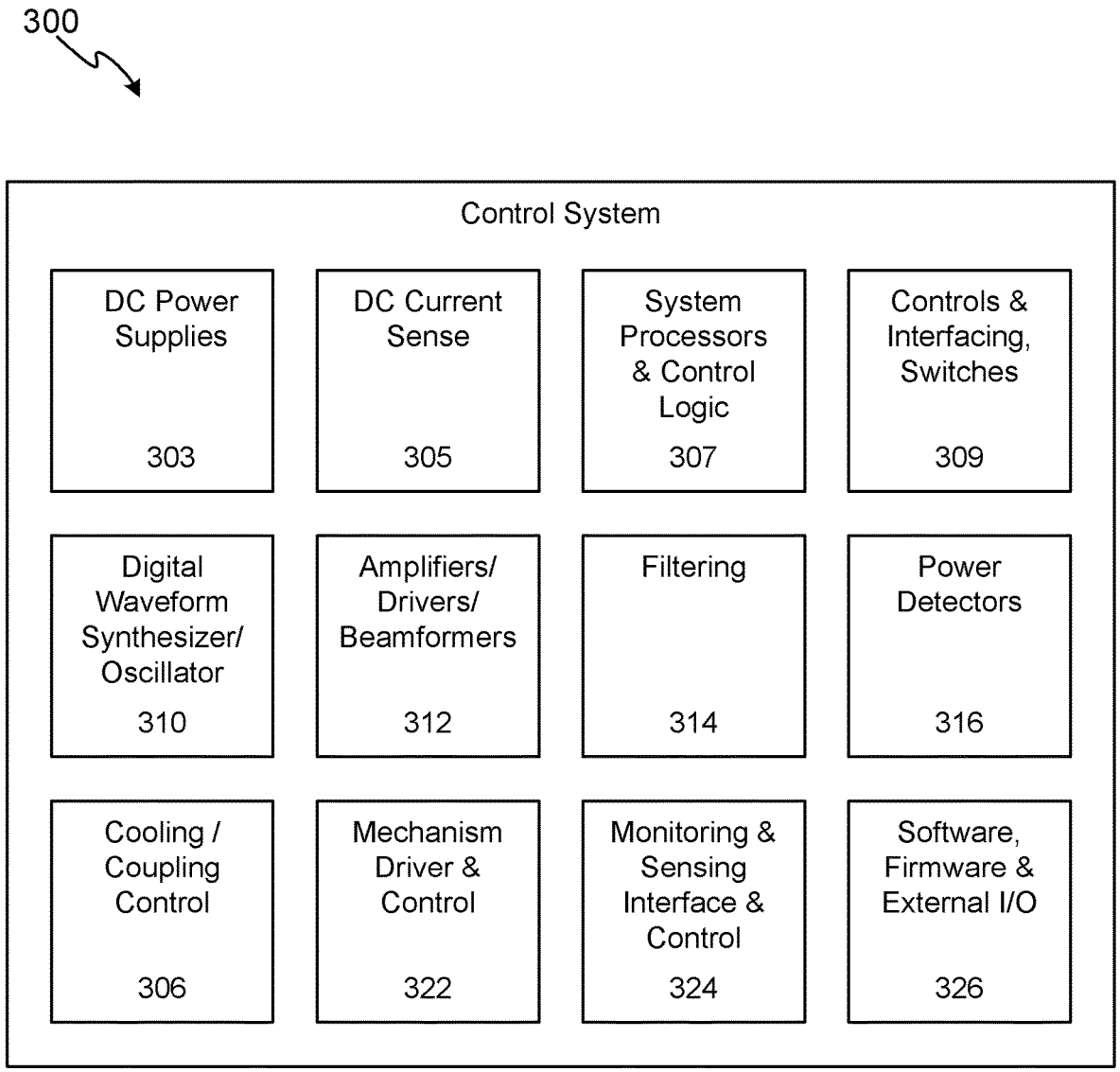

An exemplary control system 202 and display system 208 may be configured in various manners for controlling probe and system functionality for providing the various exemplary treatment methods illustrated above. For example, with reference to FIGS. 3A and 3B, in accordance with exemplary embodiments, an exemplary control system 300 can be configured for coordination and control of the entire therapeutic treatment process to achieve the desired therapeutic effect of thermal ablation to treat a sweat gland. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for controlled thermal injury of sweat glands, and the embodiments in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 204 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 200.

Cooling/coupling control systems 306 may be provided to remove waste heat from an exemplary probe 204, provide a controlled temperature at the superficial tissue interface and deeper into tissue, and/or provide acoustic coupling from transducer probe 204 to region-of-interest 206. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 204 can also be configured in various manners and comprise a number of reusable and/or disposable components and parts in various embodiments to facilitate its operation. For example, transducer probe 204 can be configured within any type of transducer probe housing or arrangement for facilitating the coupling of transducer to a tissue interface, with such housing comprising various shapes, contours and configurations. Transducer probe 204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 204 may also comprise cables and connectors; motion mechanisms, motion sensors and encoders; thermal monitoring sensors; and/or user control and status related switches, and indicators such as LEDs. For example, a motion mechanism in probe 204 may be used to controllably create multiple lesions, or sensing of probe motion itself may be used to controllably create multiple lesions and/or stop creation of lesions, e.g. for safety reasons if probe 204 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
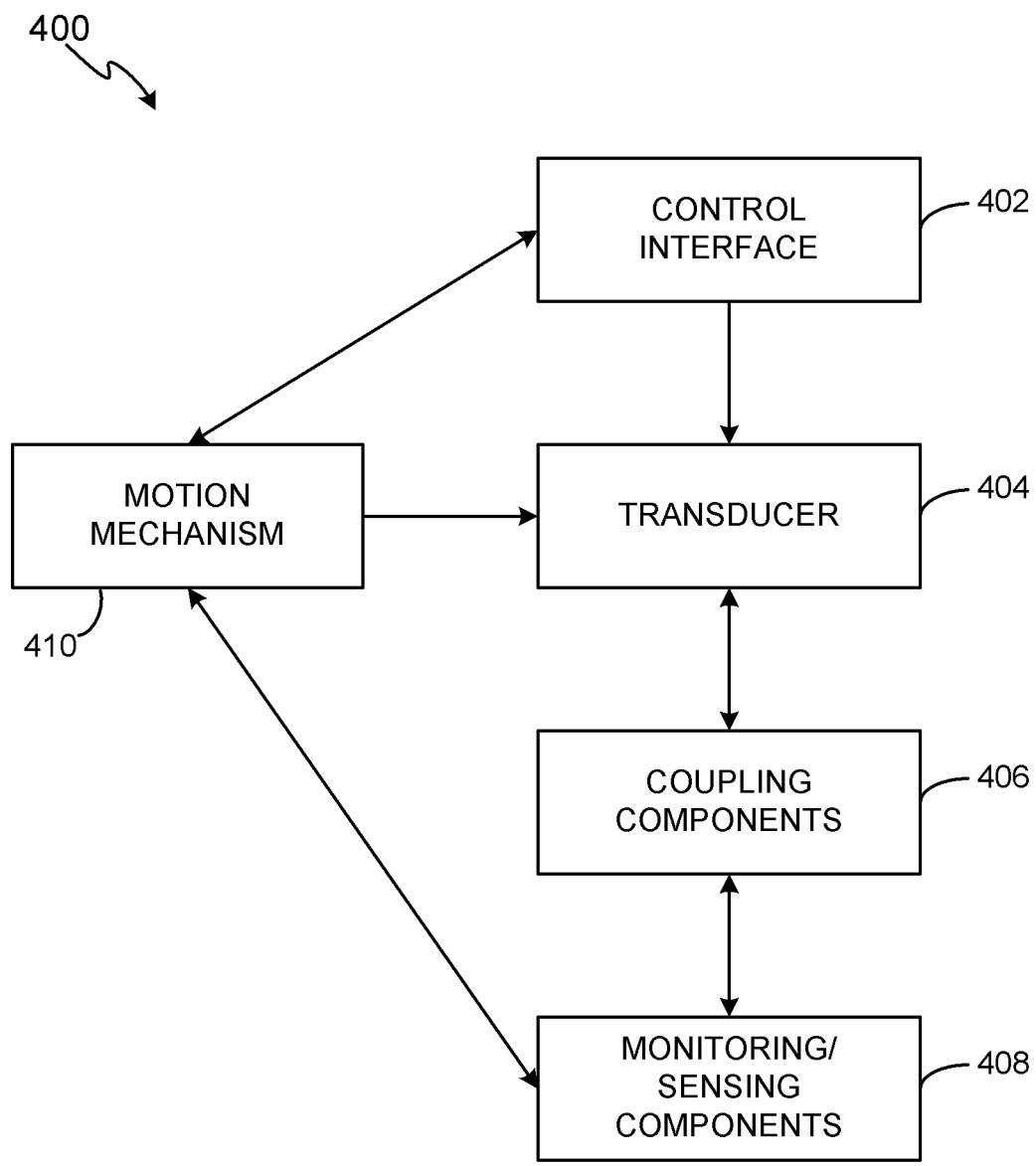
FIGS. 4A and 4B illustrate block diagrams of an exemplary probe system in accordance with exemplary embodiments of the present invention.
Figure 4B:
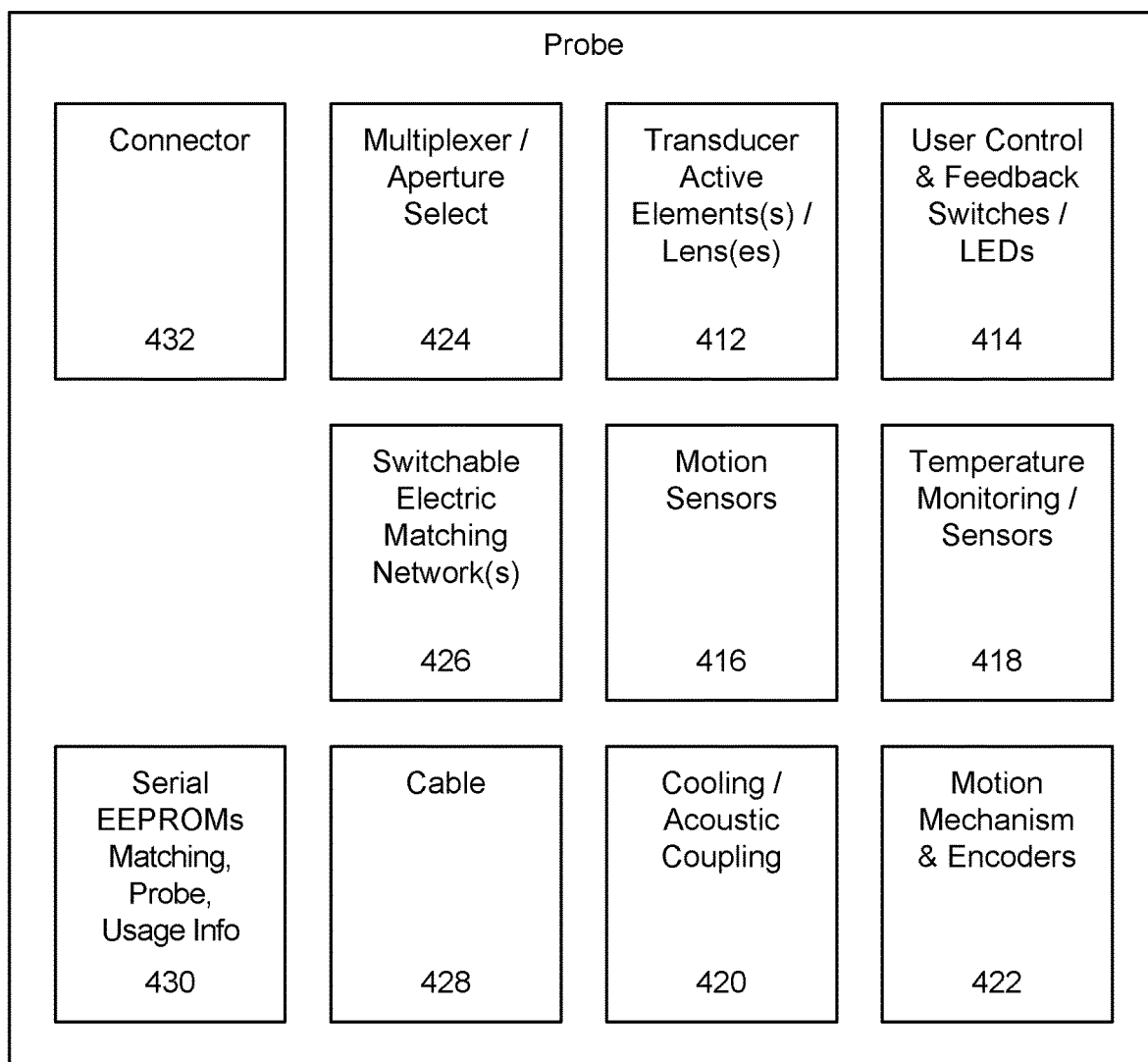

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide treatment of sweat glands, and the embodiments in FIGS. 4A and 4B are merely for illustration purposes.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430, cable 428 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or region between transducer probe 400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 400.

Figure 11:
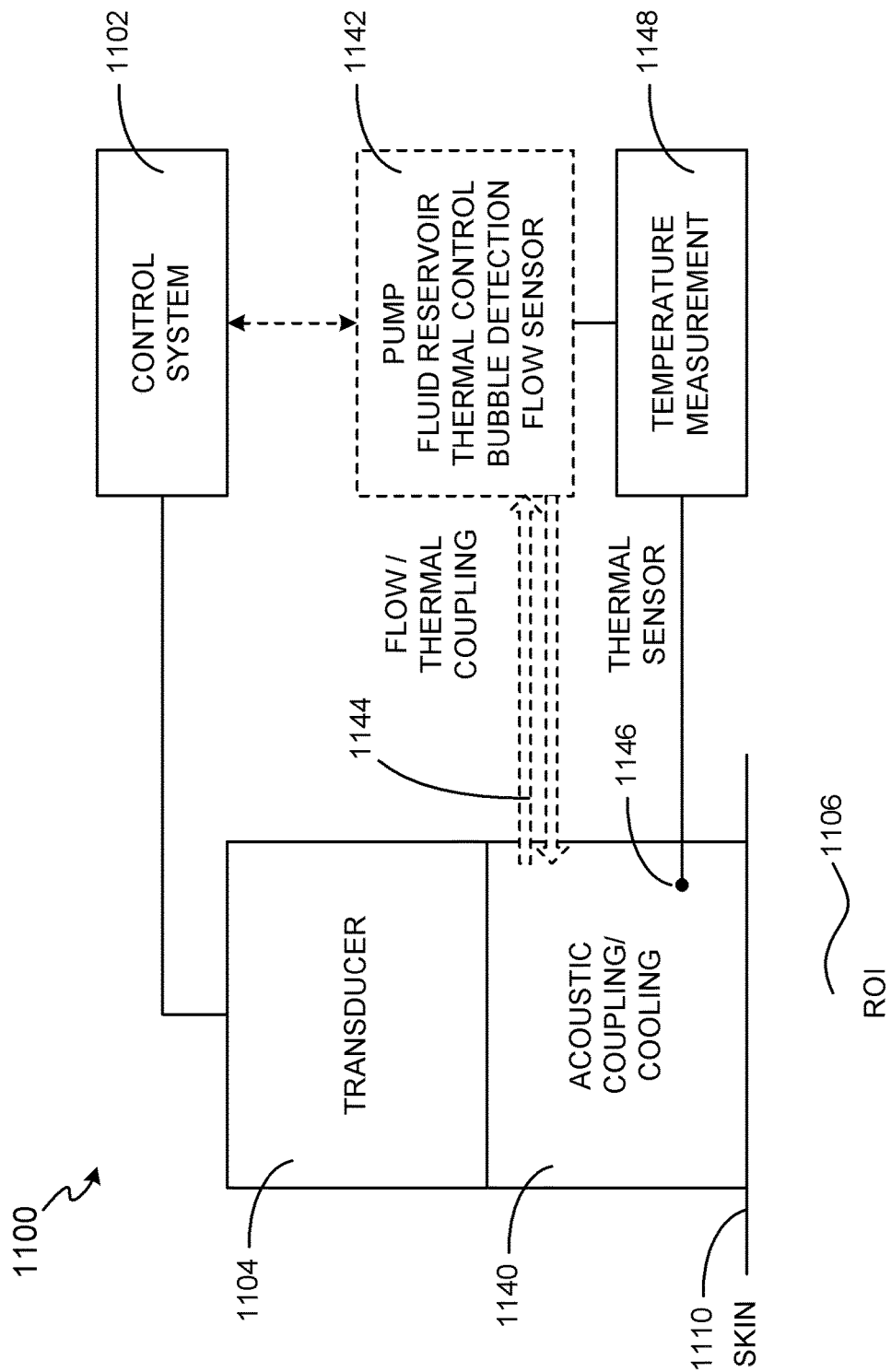
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1106 and deeper into tissue, to provide thermal control at the probe 1100 to region-of-interest interface (skin) 1110, and to remove potential waste heat from the transducer probe at region 1144. Temperature monitoring can be provided at the coupling interface via a thermal sensor 1146 to provide a mechanism of temperature measurement 1148 and control via control system 1102 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

With continued reference to FIG. 4, monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism driver 322 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for treating of sweat glands and targeted regions. Transducer 404 can also comprise one or more transduction elements and/or lenses 412. The transduction elements can comprise a piezoelectrically active material, such as lead zirconate titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of approximately 2 kHz to 75 MHz, such as for imaging applications. Transduction element 412 can also be configured with a second thickness selected to provide a center operating frequency of approximately 2 to 50 MHz, and typically between 2 MHz and 25 MHz for therapy application. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range.

Figure 5:
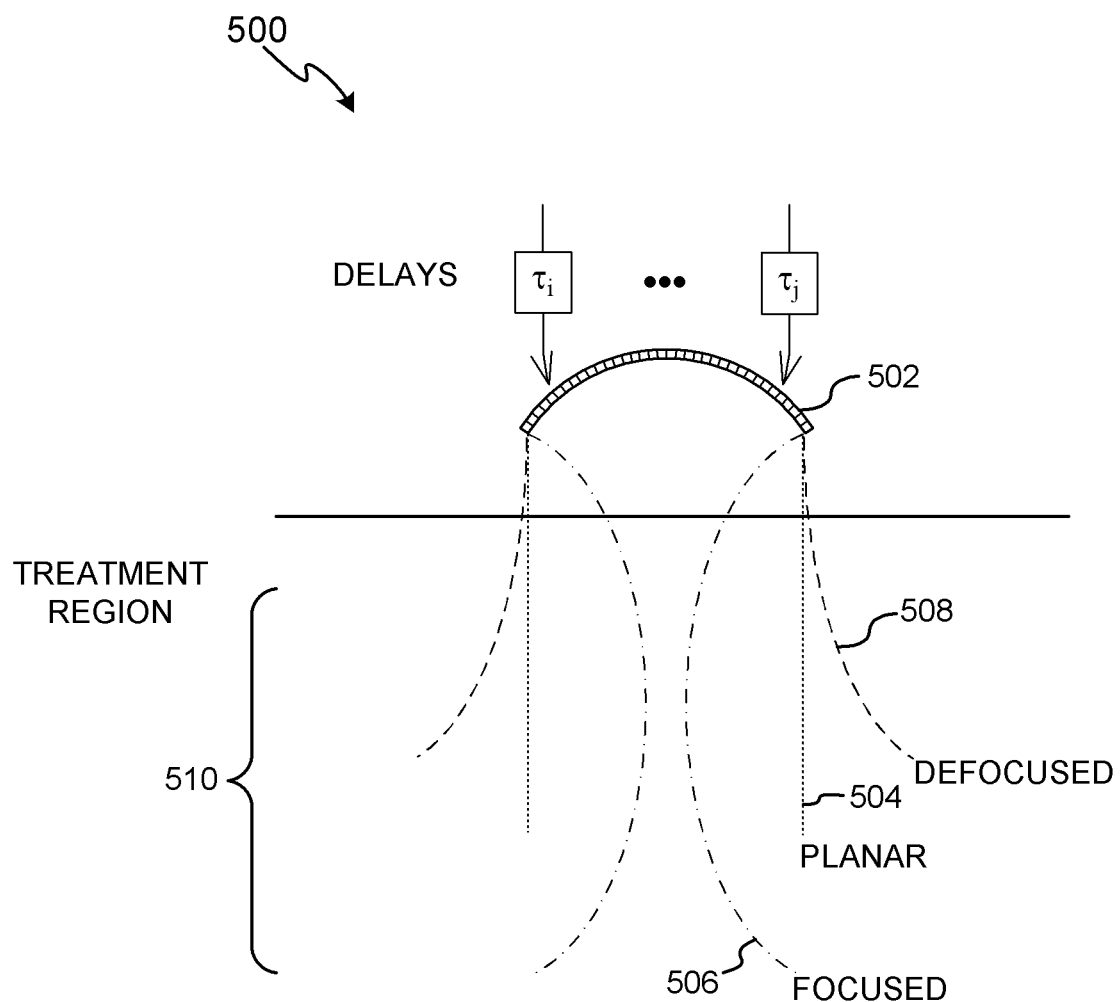
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and/or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944, 499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and/or defocus the sound field. For example, with reference to exemplary embodiments depicted in FIGS. 6A and 6B, transducer 600 may also be configured with an electronic focusing array 602 in combination with one or more transduction elements 606 to facilitate increased flexibility in treating ROI 610. Array 602 may be configured in a manner similar to transducer 502. That is, array 602 can be configured as an array of electronic apertures that may be operated by a variety of phases via variable electronic time delays, for example, T1, T2 . . . Tj. By the term "operated," the electronic apertures of array 602 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
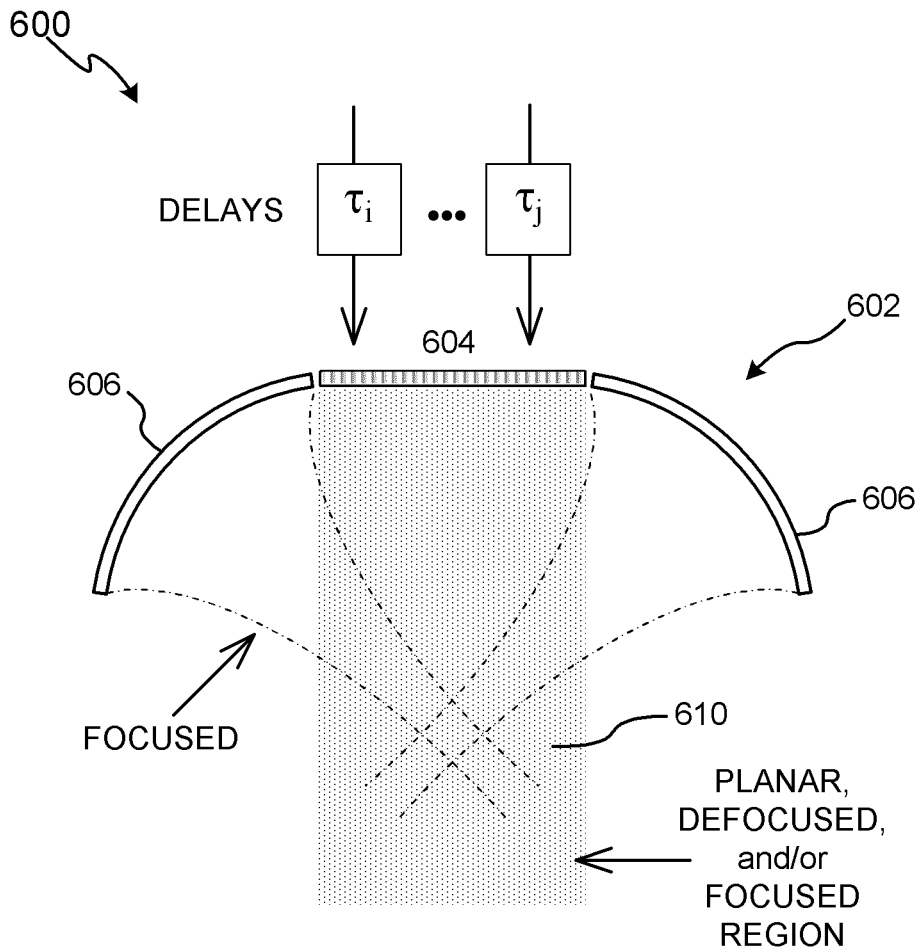
FIGS. 6A and 6B illustrate cross-sectional diagrams of an exemplary transducer in accordance with exemplary embodiments of the present invention.
Figure 6B:
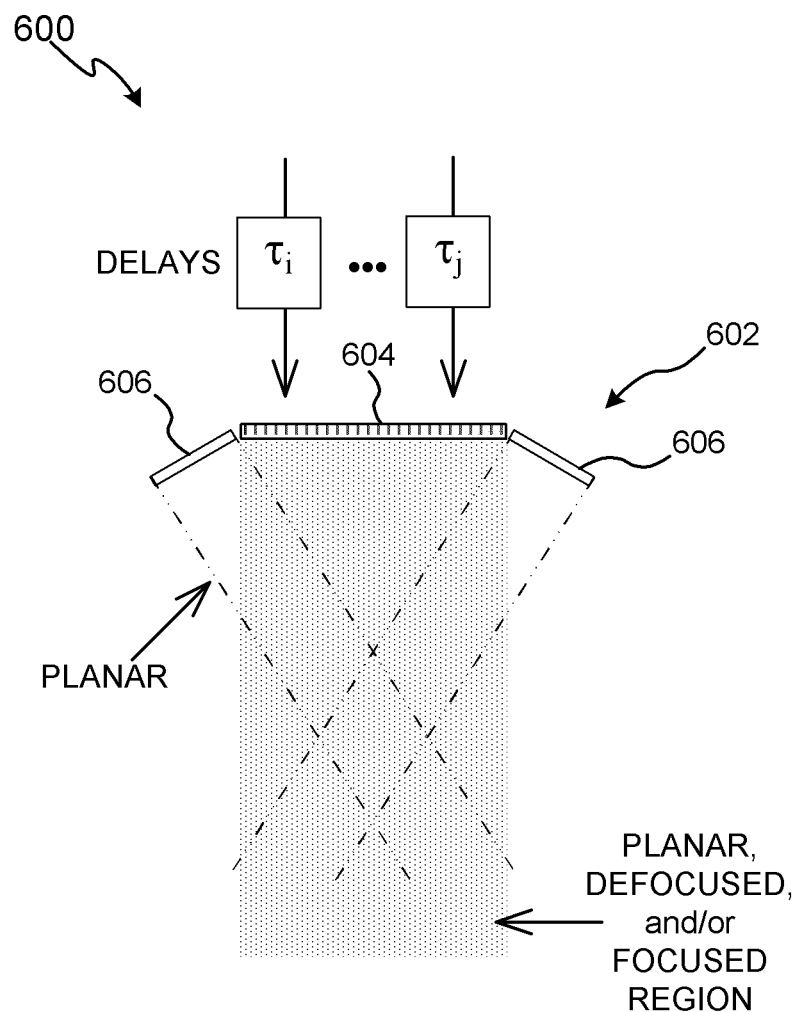

In another exemplary embodiment, depicted in FIG. 6B, transduction elements 606 can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
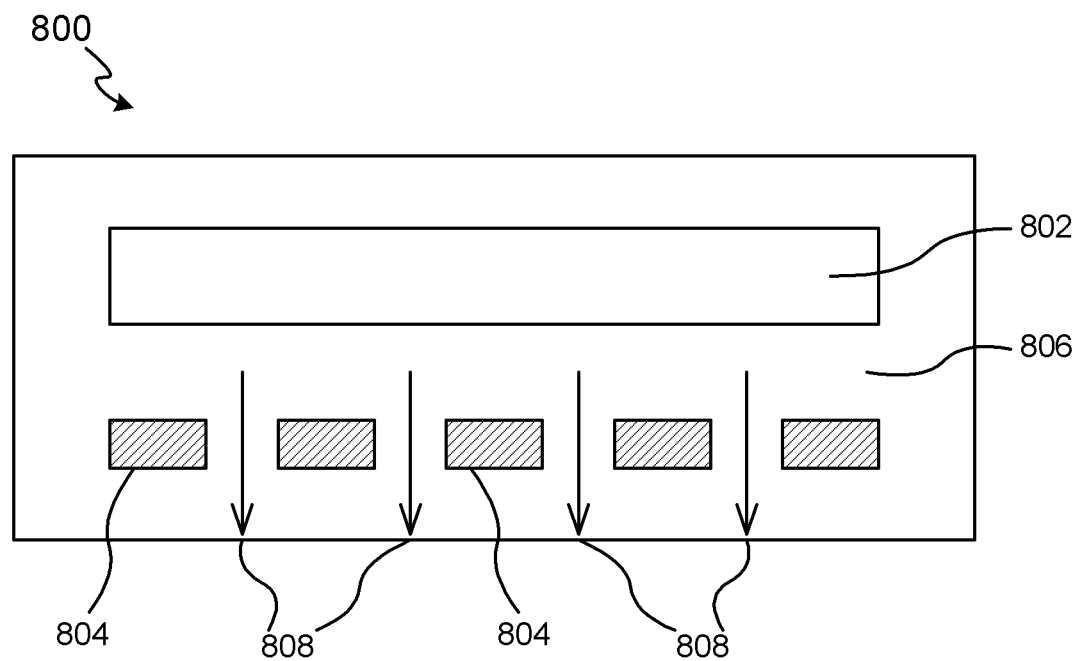
FIGS. 8A and 8B illustrate cross-sectional diagrams of an exemplary transducer in accordance with another exemplary embodiment of the present invention.
Figure 8B:
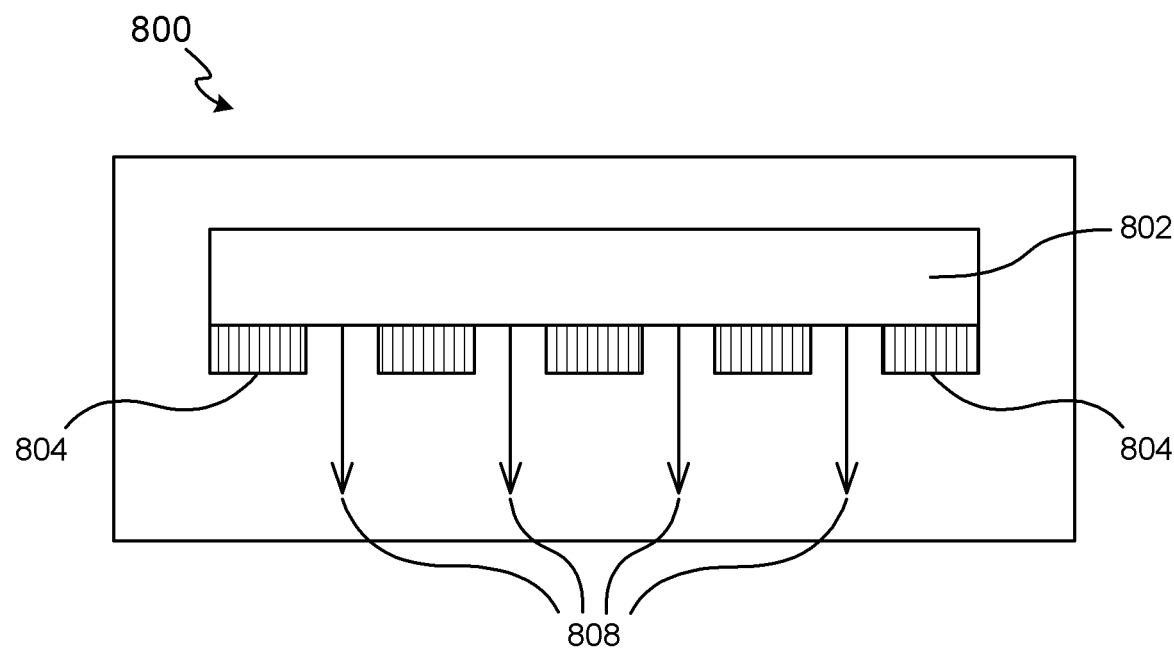

With reference to FIGS. 8A and 8B, transducer 800 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
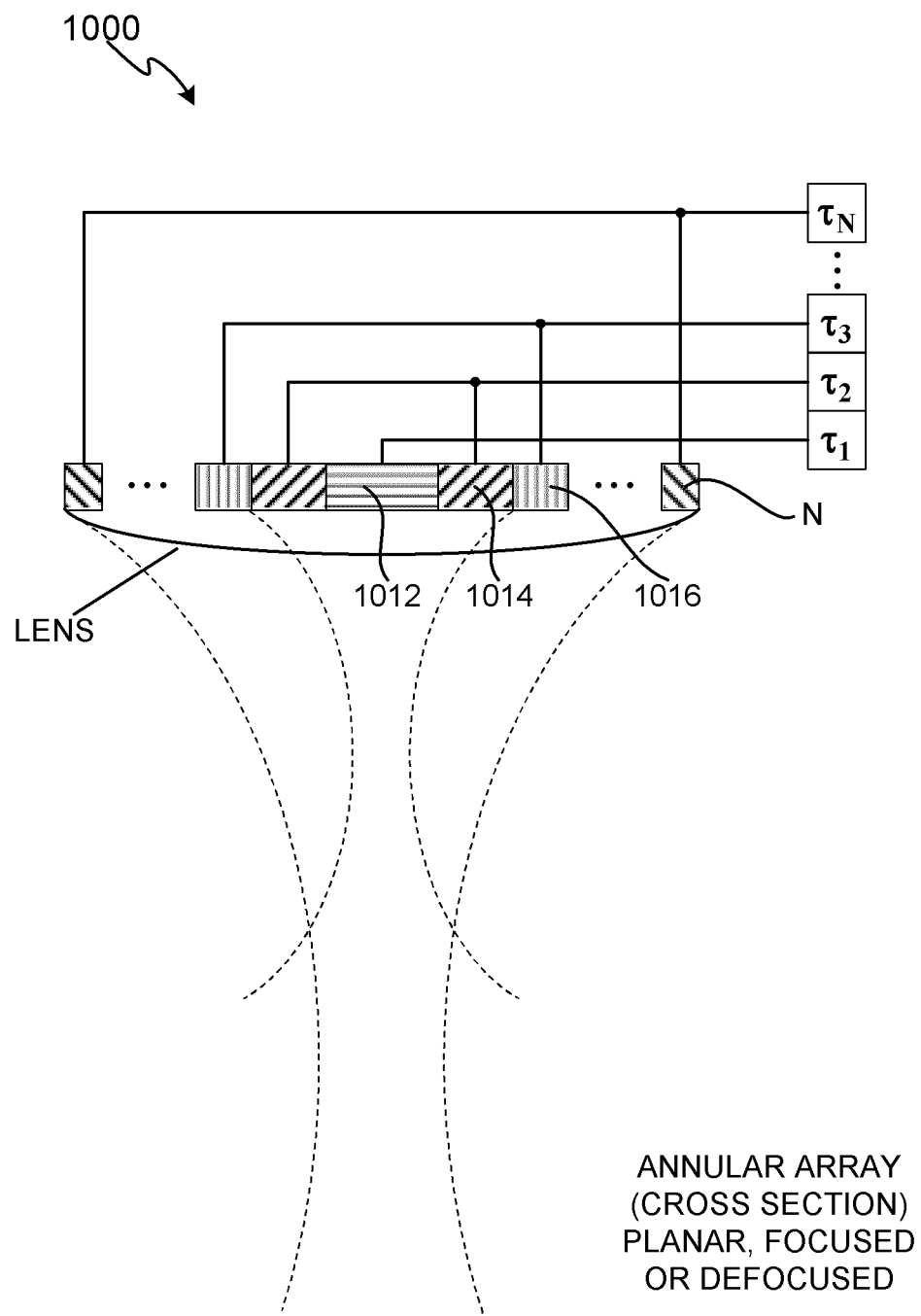
FIGS. 10A-10F illustrate cross-sectional diagrams of exemplary transducers in accordance with other exemplary embodiments of the present invention.
Figure 10B:
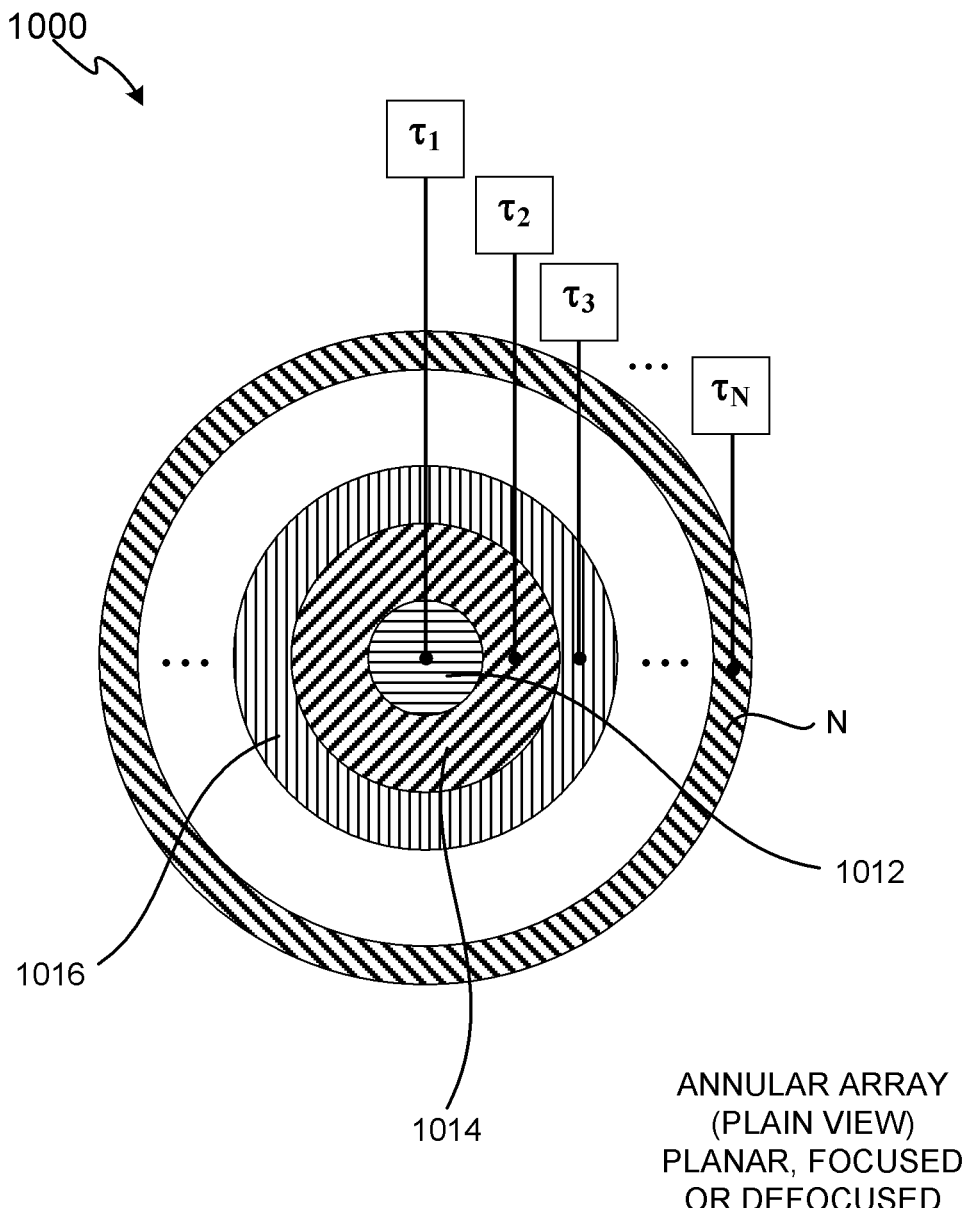
Figure 10C:
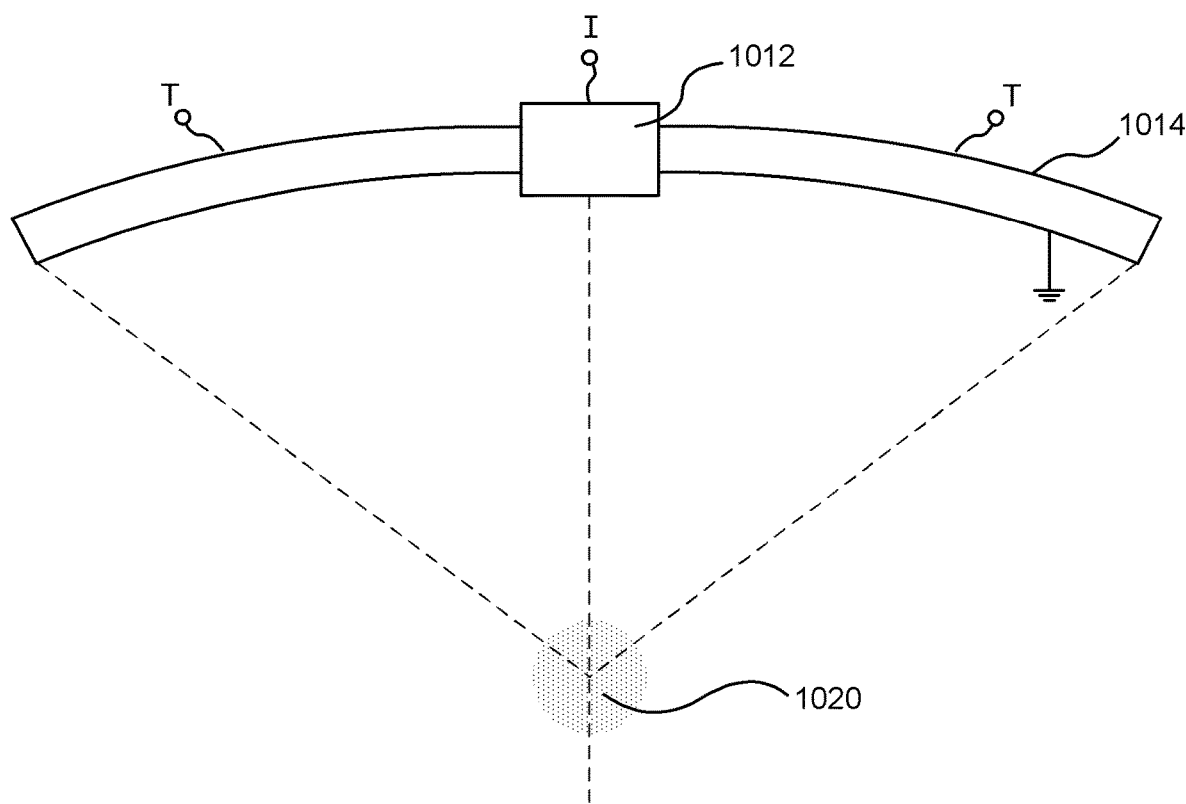
Figure 10D:
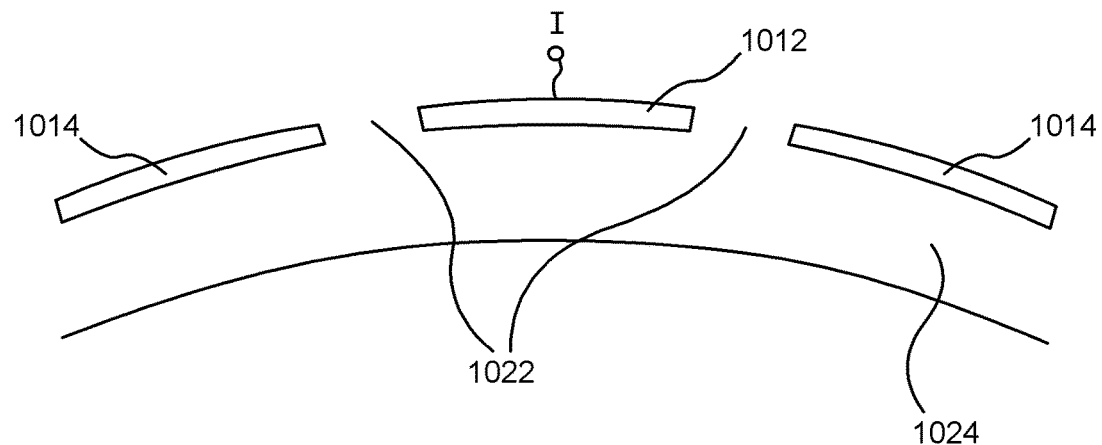
Figure 10E:
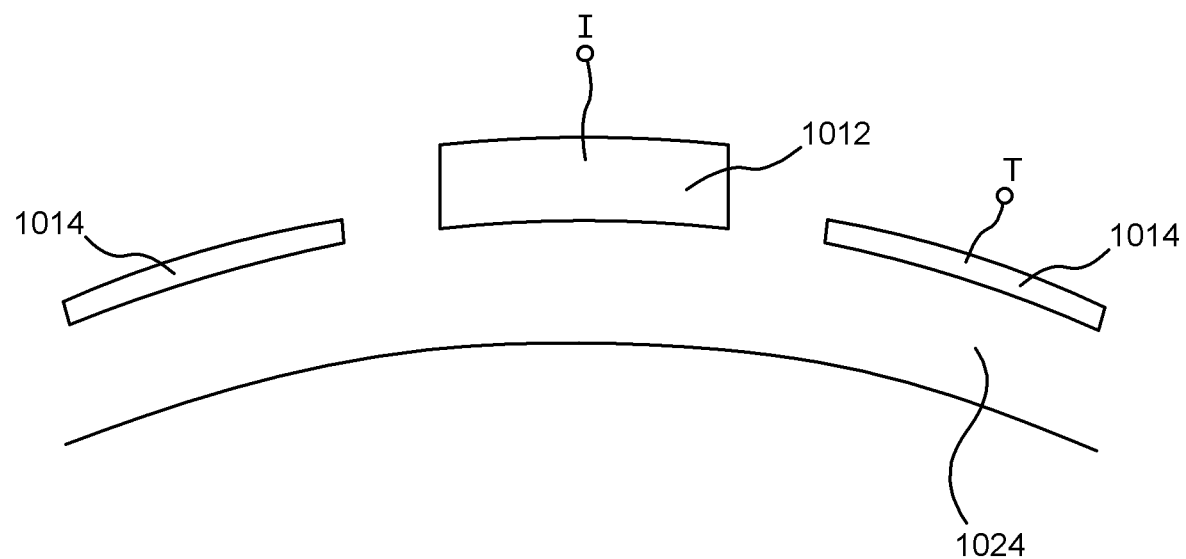

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $\tau1, \tau2, \tau3 \ldots \tau N$. An electronic focus 1020 can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 800 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with various exemplary embodiments of the present invention, transducer 404 may be configured to provide one, two and/or three-dimensional treatment applications for focusing acoustic energy to one or more regions of interest. For example, as discussed above, transducer 404 can be suitably diced to form a one-dimensional array, e.g., transducer 602 comprising a single array of sub-transduction elements.

Figure 9:
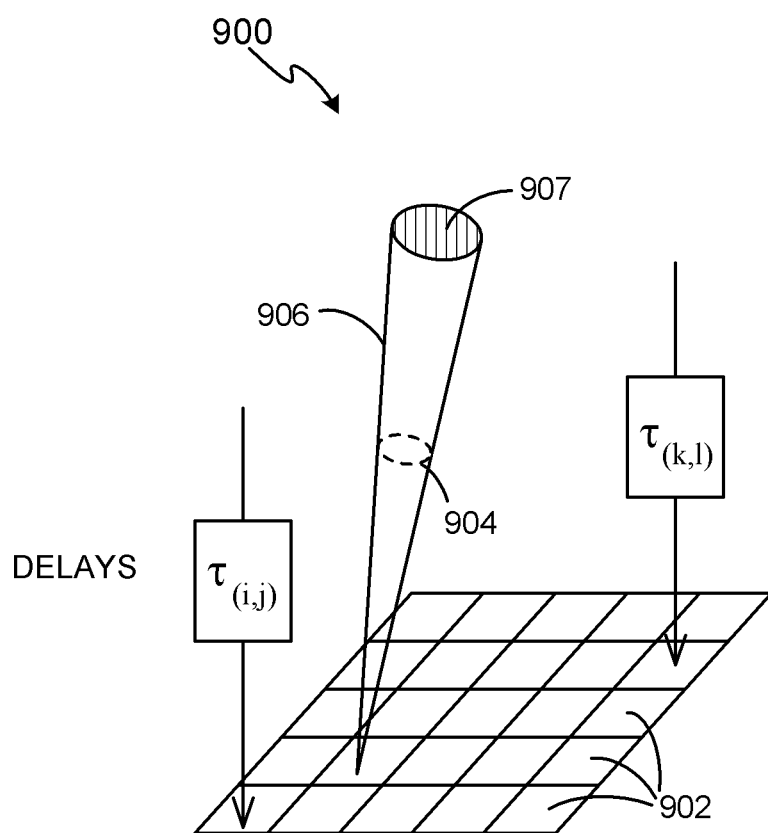
FIG. 9 illustrates an exemplary transducer configured as a two-dimensional array for ultrasound treatment in accordance with an exemplary embodiment of the present invention.

In accordance with another exemplary embodiment, transducer 404 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer 404 may be suitably configured to provide three-dimensional treatment. For example, to provide-three dimensional treatment of a region of interest, with reference again to FIG. 1, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

In accordance with other exemplary embodiments, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
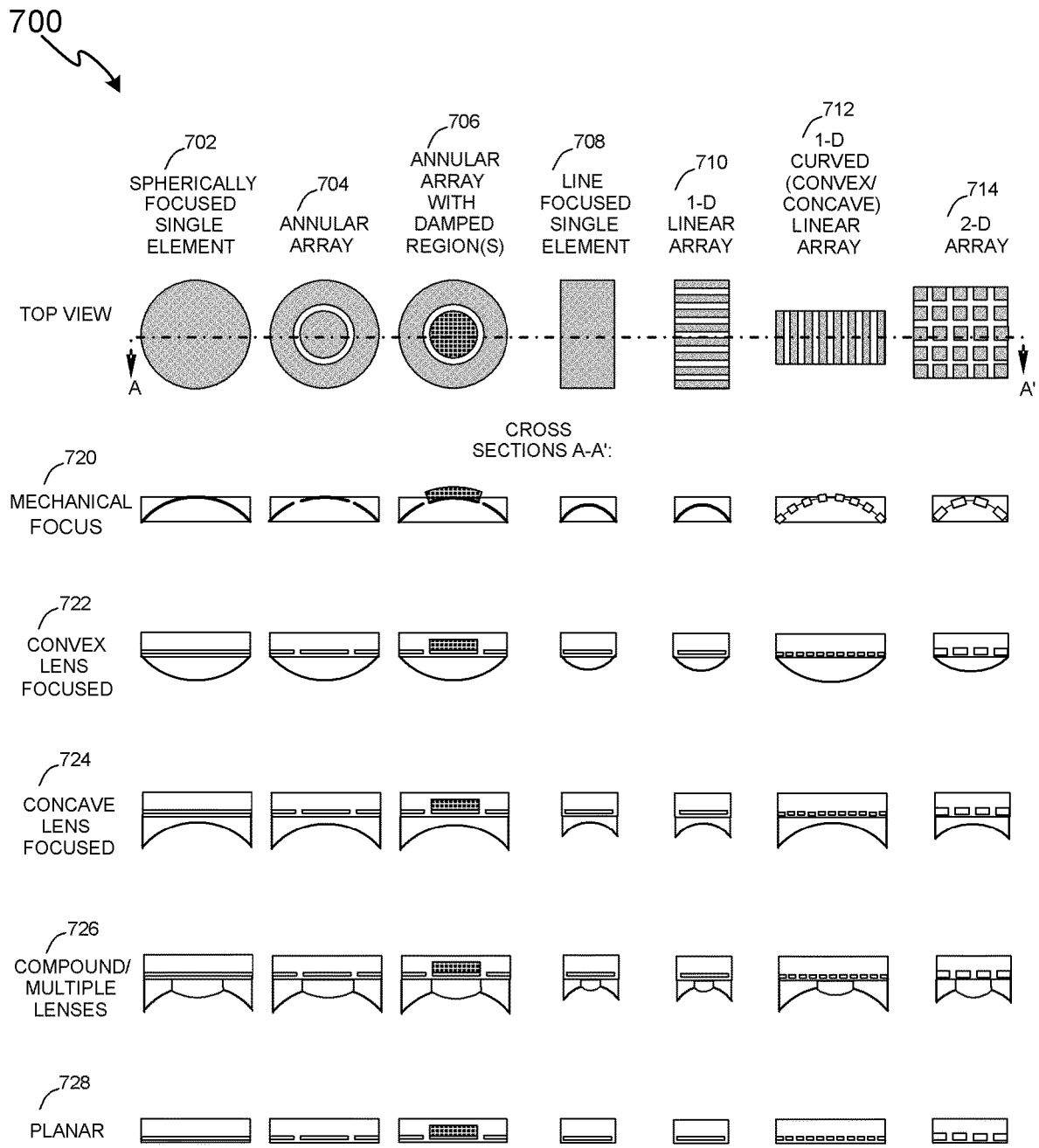
FIG. 7 illustrates exemplary transducer configurations for ultrasound treatment in accordance with various exemplary embodiments of the present invention.
Figure 10F:
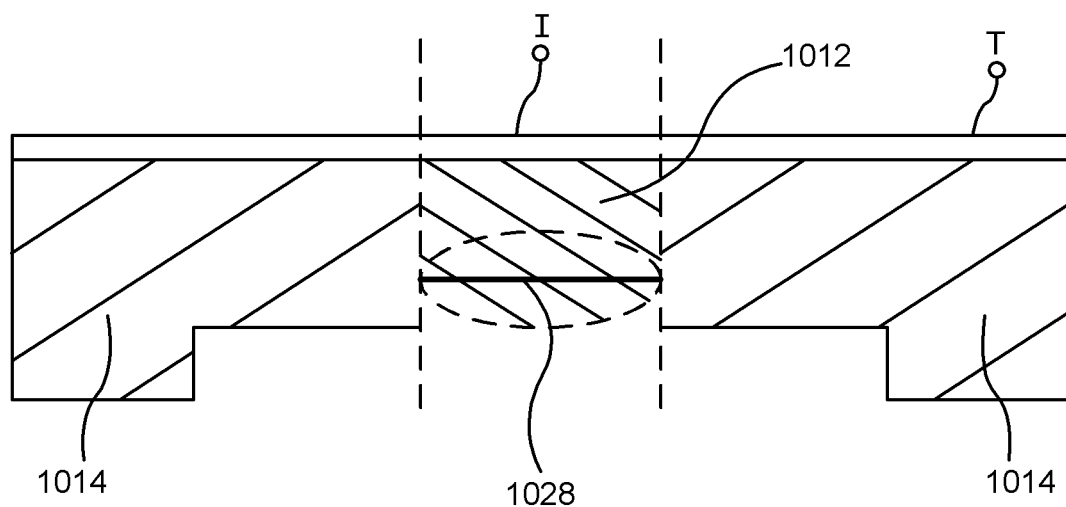

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays in concave or convex form, with or without elevation focusing 712, 2-D arrays 714, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 10C-10F.

Moreover, such transduction elements 700 may comprise a piezoelectrically active material, such as lead zirconate titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 700 may also comprise one or more matching layers configured along with the piezoelectrically active material. In addition to or instead of piezoelectrically active material, transduction elements 700 can comprise any other materials configured for generating radiation and/or acoustical energy. A means of transferring energy to and from the transducer to the region of interest is provided.

Figure 12:
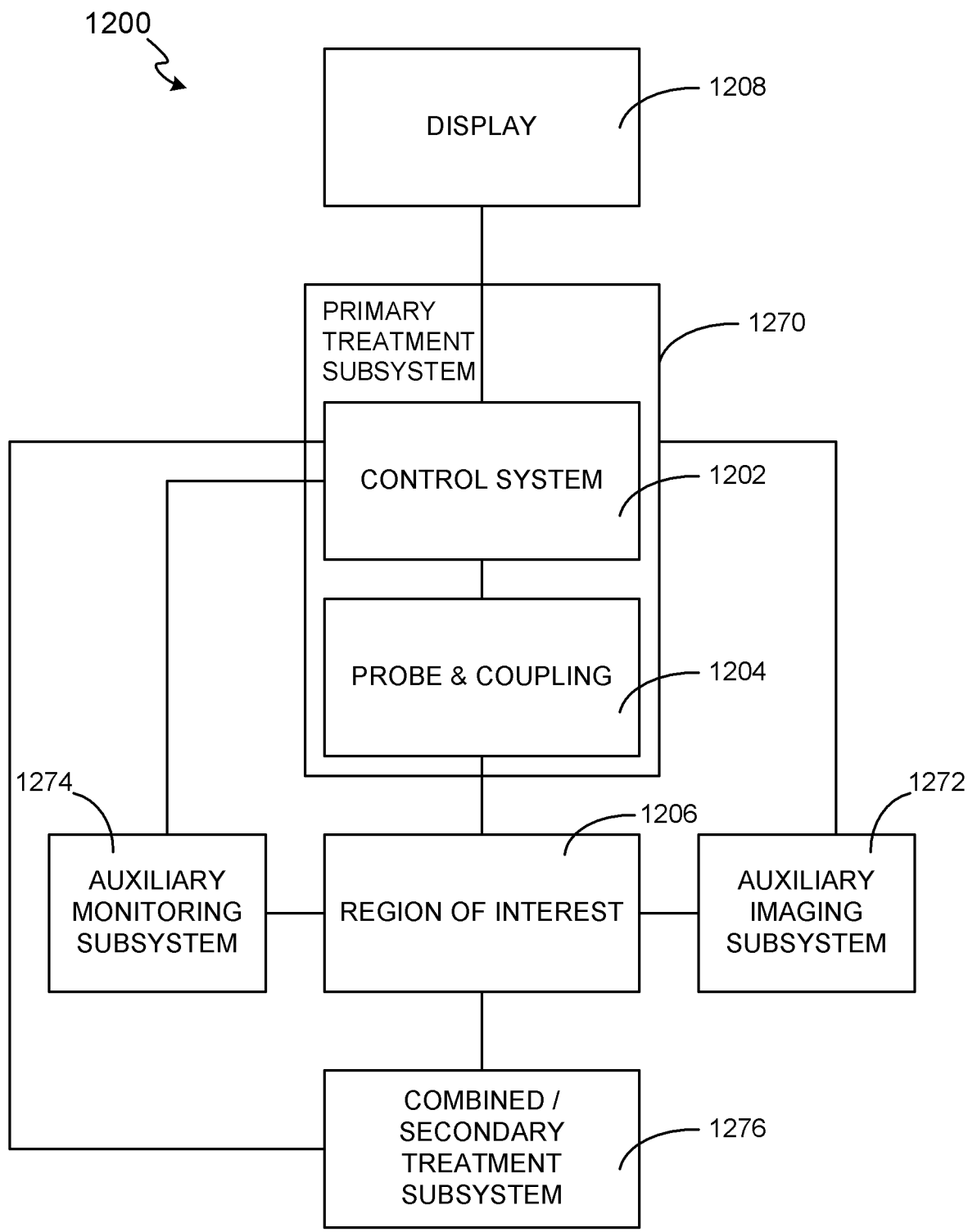
FIG. 12 illustrates a block diagram of an ultrasound treatment system combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treatment of sweat glands can comprise a control system 1206, a probe 1204, and a display 1208. For example, an exemplary treatment system 1200 for treatment of sweat glands can further comprise an auxiliary imaging subsystem 1272 and/or auxiliary monitoring modality 1274 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of the region-of-interest 1202, including imaging/monitoring enhancements. Such imaging/monitoring enhancement for ultrasound imaging via probe 1204 and control system 1206 can comprise M-mode, persistence, filtering, color, Doppler, and harmonic imaging among others; furthermore an ultrasound treatment system 1270, as a primary source of treatment, may be combined with a secondary treatment subsystem 1276, including radio frequency (RF), intense pulsed light (IPL), laser, infrared laser, microwave, or any other suitable energy source.

Figure 13:
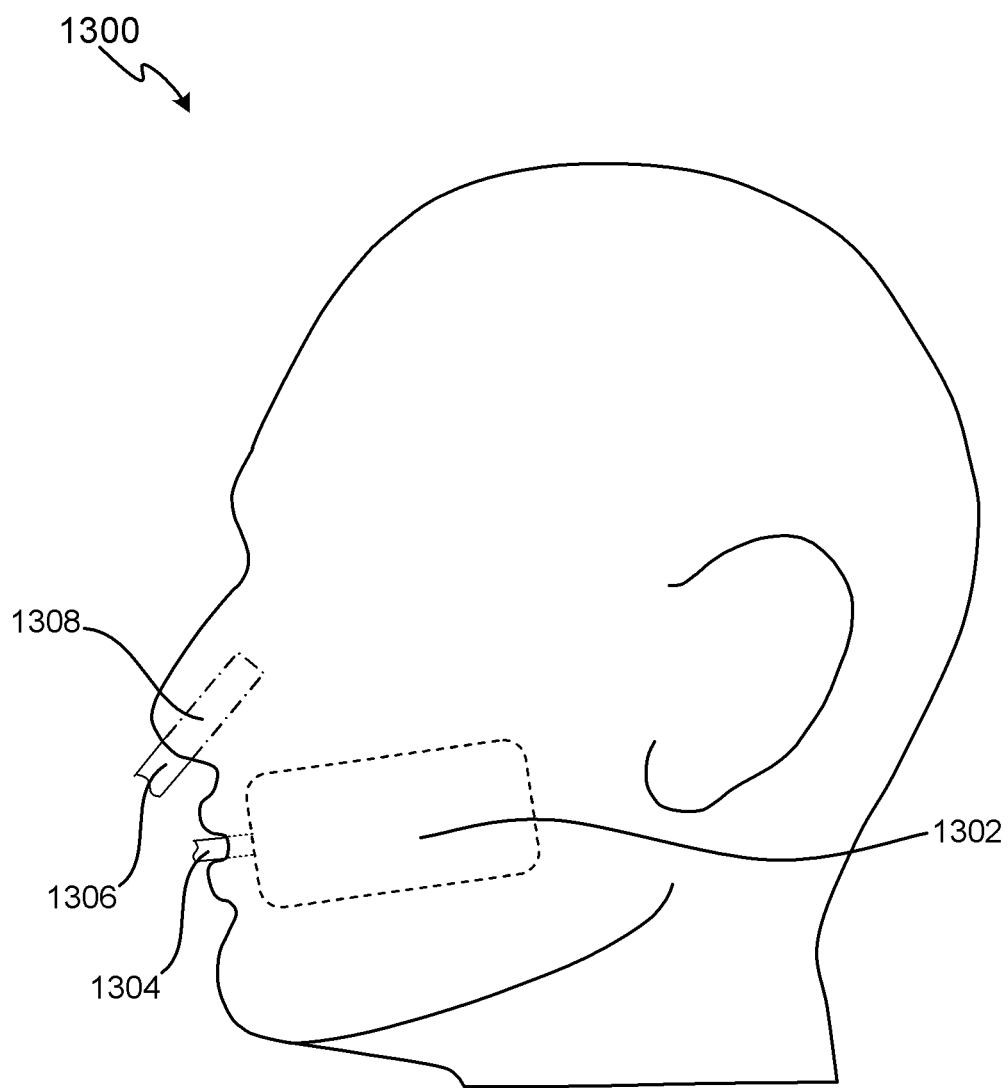
FIG. 13 illustrates a schematic diagram with imaging, therapy, or monitoring being provided with one or more active or passive oral inserts in accordance with an exemplary embodiment of the present invention.

In accordance with another exemplary embodiment, with reference to FIG. 13, treatment composed of imaging, monitoring, and/or therapy to a region of interest 1302 and/or 1308 may be aided, augmented, and/or delivered with passive or active devices 1304 and/or 1306 within the oral and/or nasal cavity, respectively. For example, if passive or active device 1304 and/or 1306 are second transducers or acoustic reflectors acoustically coupled to the mucous membranes it is possible to obtain through transmission, tomographic, or round-trip acoustic waves which are useful for treatment monitoring, such as in measuring acoustic speed of sound and attenuation, which are temperature dependent; furthermore such transducers could be used to treat and/or image. In addition an active, passive, or active/passive object 1304 and/or 1306 may be used to flatten the skin, and/or may be used as an imaging grid, marker, or beacon, to aid determination of position. A passive or active device 1304 and/or 1306 may also be used to aid cooling or temperature control. Natural air in the oral cavity and/or nasal cavity may also be used as passive device 1304 and/or 1306 whereby it may be utilized to as an acoustic reflector to aid thickness measurement and monitoring function.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

What is claimed is:

1. A method for ultrasound treatment of a skin gland, the method comprising:
    positioning a probe on a skin surface, the probe comprising a piezoelectric ultrasound therapy element;
    targeting a region of interest under the skin surface, wherein the region of interest comprises a gland selected from the group consisting of: a sebaceous gland and a sweat gland,
    wherein the sweat gland is further selected from the group consisting of: an apocrine gland and an eccrine gland; and
    using the piezoelectric ultrasound therapy element to thermally treat the gland in the region of interest to reduce a secretion from said gland,
    wherein the piezoelectric ultrasound therapy element is configured to deliver energy at a frequency in a range of 500 kHz to 15 MHz to a depth of 1 mm to 7 mm below the skin surface to heat the gland.

2. The method of claim 1, wherein the piezoelectric ultrasound therapy element delivers focused ultrasound energy at the frequency in the range of 500 kHz to 15 MHz.

3. The method of claim 1, wherein the using the piezoelectric ultrasound therapy element comprises ablating at least a portion of the gland in the region of interest.

4. The method of claim 1, wherein the using the piezoelectric ultrasound therapy element comprises shocking the gland to reduce the secretion from the gland.

5. The method of claim 1, wherein the using the piezoelectric ultrasound therapy element comprises adjustable control of spatial parameters and temporal parameters of the probe to generate conformal lesions of specifically targeted shapes, sizes or orientations in at least a portion of the region of interest.

6. The method of claim 1, wherein the using the piezoelectric ultrasound therapy element comprises using a motion mechanism coupled to the piezoelectric ultrasound therapy element to position the piezoelectric ultrasound therapy element within the probe.

7. The method of claim 1, wherein the using the piezoelectric ultrasound therapy element comprises using electronic phase focusing of the piezoelectric ultrasound therapy element to position a focus for delivery of the energy to create a thermal lesion in the gland.

8. The method of claim 1, further comprising creating a plurality of thermal lesions by producing a discrete locus of spaced conformal lesions based on control of spatial parameters and temporal parameters to treat any one of the group consisting of: acne and sweating.

9. The method of claim 1, wherein the probe comprises a plurality of piezoelectric ultrasound therapy elements.

10. The method of claim 1, further comprising monitoring a region treated by the piezoelectric ultrasound therapy element for further planning, assessing of results, or providing feedback.

11. The method of claim 1, further comprising administering a pharmaceutical agent to the region of interest to further reduce the secretion from the gland.

12. The method of claim 1, wherein the region of interest consists of the sweat gland, wherein the sweat gland is located an area selected from the group consisting of one or more of the following: a face, an armpit, a palm, and a sole.

13. A method for thermal treatment with focused ultrasound of a skin gland, the method comprising:
    identifying a plurality of glands in a skin of a subject, wherein the plurality of glands comprise at least one of the group consisting of: a sebaceous gland and a sweat gland, wherein the sweat gland is one of the group consisting of: an apocrine gland and an eccrine gland;
    placing a thermal energy delivery probe on a skin surface overlying the plurality of glands;
    activating the thermal energy device via targeting the thermal energy at a frequency in a range of 500 kHz to 15 MHz, via the energy delivery probe, through the skin surface to the plurality of glands using an automated motion mechanism.

14. The method of claim 13, further comprising delivering the energy, via at least one piezoelectric therapy element, wherein the energy comprises ultrasound energy and wherein the at least one piezoelectric therapy element is focused with at least one of the group consisting of a spherical focus and a cylindrical focus.

15. The method of claim 13, further comprising imaging the plurality of glands with a piezoelectric imaging transducer.

16. A method for treating a skin gland, the method comprising:
- transmitting energy at a frequency in a range of 500 kHz to 15 MHz, via at least one piezoelectric ultrasound therapy element, to deliver a thermal energy to a first skin gland; and
- moving the at least one piezoelectric ultrasound therapy element, via an automatic motion mechanism, to deliver a thermal energy to a second skin gland,
- wherein the at least one piezoelectric ultrasound therapy element is configured with at least one of the group consisting of a spherical focus and a cylindrical focus,
- wherein the thermal energy reduces an amount of secretion produced from the first and second skin glands;
- wherein the first skin gland is selected among the group consisting of: a sebaceous gland, an apocrine gland and an eccrine gland, and
- wherein the second skin gland is selected among the group consisting of: a sebaceous gland, an apocrine gland and an eccrine gland.

17. The method of claim 16, wherein the energy comprises focused ultrasound energy.

18. The method of claim 16, further comprising imaging at least the first skin gland with a piezoelectric ultrasound imaging element.

19. The method of claim 16, wherein the first and second skin glands are at least partially ablated to reduce bacteria in a secretion from at least one of the first skin gland and the second skin gland.

20. The method of claim 16, wherein the treatment comprises at least one of the group consisting of: sweat reduction and acne reduction.

* * * * *